(12) United States Patent
Shapiro (10) Patent No.: US 11,717,696 B2
(45) Date of Patent: Aug. 8, 2023

(54) MAGNETICALLY-ASSISTED DELIVERY INTO AND THROUGH THE SKIN (71) Applicant: OTOMAGNETICS, INC., Rockville, MD (US)

(72) Inventor: Benjamin Shapiro, Washington, DC (US)

(73) Assignee: Otomagnetics, Inc., Gaithersburg, MD (US)

(*) Notice: Subject to any disclaimer, the term of this patent is extended or adjusted under 35 U.S.C. 154(b) by 120 days.

(21) Appl. No.: 16/760,840

(22) PCT Filed: Oct. 31, 2018

(86) PCT No.: PCT/US2018/058572
§ 371 (c)(1),
(2) Date: Apr. 30, 2020

(87) PCT Pub. No.: WO2019/089843
PCT Pub. Date: May 9, 2019

(65) Prior Publication Data
US 2021/0213299 A1 Jul. 15, 2021

Related U.S. Application Data (60) Provisional application No. 62/579,544, filed on Oct. 31, 2017.

(51) Int. Cl.
A61N 2/00 (2006.01)
A61M 37/00 (2006.01)
A61N 2/06 (2006.01)

(52) U.S. Cl.
CPC ............. *A61N 2/002* (2013.01); *A61M 37/00* (2013.01); *A61N 2/06* (2013.01); *A61M 2037/0007* (2013.01)

(58) Field of Classification Search
CPC . A61N 2/002; A61N 2/06; A61N 2/02; A61N 2/004; A61N 2/008; A61N 2/00
See application file for complete search history.

(56) References Cited

U.S. PATENT DOCUMENTS 4,822,617 A 4/1989 Panoz
5,244,677 A 9/1993 Kreckel et al.
(Continued)

FOREIGN PATENT DOCUMENTS

EP 3013287 B1 6/2020
JP S59155268 A 9/1984
(Continued)

OTHER PUBLICATIONS

International Search Report and Written Opinion for corresponding PCT Application No. PCT/US2018/058572, dated Jan. 17, 2019.
(Continued)

*Primary Examiner* — Samuel G Gilbert
(74) *Attorney, Agent, or Firm* — Wilson Sonsini Goodrich & Rosati (57) ABSTRACT A method for treating a patient includes providing a delivery device capable of generating a magnetic field, placing the device above or below the skin, and directing the agent into the patient's skin via the device. The therapeutic agent is directed to a treatment site through the skin. Systems for directing agents are also included herein.

14 Claims, 9 Drawing Sheets (56) References Cited

U.S. PATENT DOCUMENTS

| | | | |
|---|---|---|---|
| 9,186,317 B2 * | 11/2015 | Smyth | A61K 41/0052 |
| 9,463,330 B2 | 10/2016 | Edwards | |
| 10,646,454 B2 * | 5/2020 | Liu | A61K 9/7084 |
| 2002/0127722 A1 | 9/2002 | Kuehnle | |
| 2007/0190123 A1 | 8/2007 | Aida et al. | |
| 2009/0093669 A1 * | 4/2009 | Farone | A61K 31/16 514/447 |
| 2009/0287036 A1 | 11/2009 | Shapiro | |
| 2010/0212676 A1 | 8/2010 | Shapiro et al. | |
| 2011/0060320 A1 | 3/2011 | Aharon-Attar | |
| 2014/0336616 A1 * | 11/2014 | Edwards | A61N 2/002 604/173 |
| 2017/0197070 A1 | 7/2017 | Masri et al. | |
| 2017/0197071 A1 | 7/2017 | Gottenbos | |
| 2018/0280674 A1 | 10/2018 | Shapiro | |

FOREIGN PATENT DOCUMENTS

| | | | |
|---|---|---|---|
| JP | H08509200 A | 10/1996 | |
| JP | 2013534842 A | 9/2013 | |
| JP | 2017527528 A | 9/2017 | |
| WO | 2005072669 A1 | 8/2005 | |
| WO | 2009000478 A1 | 12/2009 | |
| WO | 2016069982 A1 | 5/2016 | |

OTHER PUBLICATIONS

Pangburn, Nanoparticle Drug Patches Will Deliver Cancer Treatment Without Needles (Jul. 11, 2013); https://www.vice.com/en/article/kbbdgz/nanoparticle-drug-patches-will-deliver-cancer-treatment-without-needles.

Sun et al., Stimuli-Responsive Biodegradable Hyperbranched Polymer—Gadolinium Conjugates as Efficient and Biocompatible Nanoscale Magnetic Resonance Imaging Contrast Agents, ACS Appl. Mater. Interfaces (Apr. 4, 2016); 8(16)10499-10512.

Supplementary European Search Report for corresponding European Patent Application No. EP18871946.2, dated Jan. 24, 2017.

* cited by examiner

1. Permanent magnet
2. Magnetic field lines
3. Region of strong magnetic field
4. Region of weaker magnetic field
5. Force on and motion direction of iron particles
6A. Chain of iron particles (oriented along motion)
6B. Chain of iron particles (oriented mostly perpendicular to motion)

MAGNETICALLY-ASSISTED DELIVERY INTO AND THROUGH THE SKIN

CROSS REFERENCE TO RELATED APPLICATIONS

This application is filed pursuant to 35 U.S.C. §371 as a United States National Phase Application of International Application Ser. No. PCT/US2018/058572, filed Oct. 31, 2018, which claims priority on U.S. Provisional Patent Application No. 62/579,544, filed on Oct. 31, 2017, which is incorporated by reference herein in its entirety and for all purposes.

TECHNICAL FIELD

This application relates generally to the delivery of agents into and/or through the skin of a mammal. More specifically, this application relates to the delivery of therapeutic agent, pharmaceutical agents, molecular agents, nucleotides, or proteins into and/or through skin and their use in allowing such therapeutic agents to be administered into and/or through skin.

BACKGROUND

Figure 1:
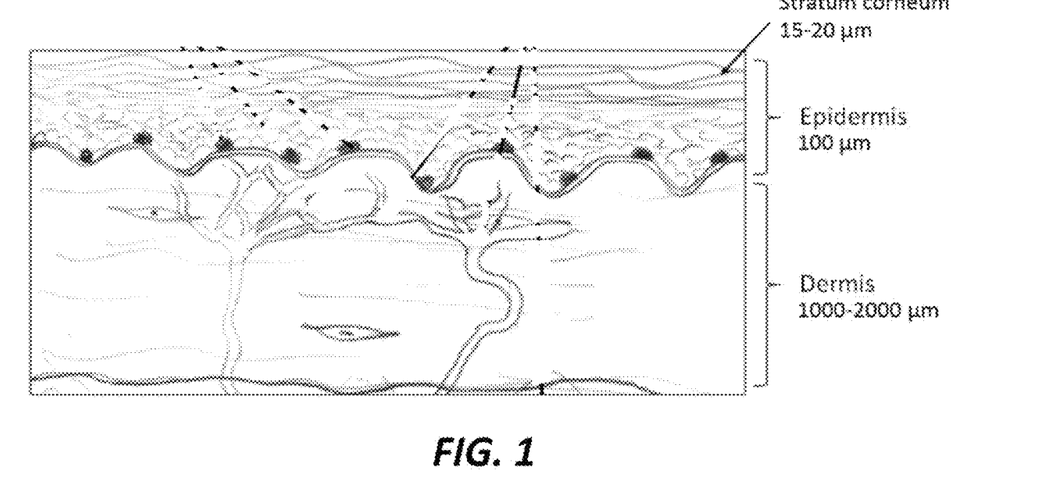
FIG. 1 shows a microscopic view of skin.

Skin is the protective covering, and it has evolved to prevent foreign materials from entering the body. FIG. 1 shows the layers of the skin, and the skin prevents efficient delivery of drugs into, and across, it. Because of these barriers, through skin drug delivery is achieved by a hypodermic needle injection. Such injections have two serious disadvantages: pain and needle phobia, and also transmission of infectious diseases which can occur due to needle reuse and the injury caused to the skin. The outermost layer, the Stratum Corneum, is 15-20 micrometers thick and is composed of dead corneocytes locked in a lipid matrix. Below that lies the viable Epidermis (100 μm thick), compromised of keratinocytes. Tight cell-to-cell junctions seal adjacent epithelial cells to each other, thus making it difficult for drugs to enter the skin. Below that is the Dermis layer, which is 1-2 mm thick (1,000-2,000 μm). The skin has evolved and is designed to keep material from entering the body, together these layers of the skin form a formidable barrier to drug delivery.

US Patent Publication No. 20140073835 is directed to methods for pushing an active agent into a patient's ear compartments using magnetic forces. This disclosure does not disclose using magnetic forces to direct agents into and through skin.

Accordingly, there is need for improved methods for delivering agents into and through the skin. It is to this need, among others, that this application is directed.

SUMMARY

This application discloses a method for treating a patient comprising: (a) providing a delivery device capable of generating a magnetic field; (b) placing the device above or below the skin; and (c) directing the agent into the patient's skin via the device. The therapeutic agent is directed to a treatment site through the skin.

This application also discloses a skin patch that combines magnetic injector devices and magnetic nanoparticles into at least one patch that can be glued/adhered onto the skin and then delivers the particles into and through the skin.

DEFINITIONS

The terms "therapy" and "treatment" as used herein interchangeably, cover any treatment of a disease or disorder, and includes, for example, curing the disease or disorder, preventing the disease or disorder from occurring in a subject which may be predisposed to the disease but has not yet been diagnosed with the disease or disorder, inhibiting the disease or disorder, relieving the disease or disorder, providing a prophylactic effect, evolving a beneficial immunological effect; and improving the quality of life of a subject afflicted by a disease or disorder.

DETAILED DESCRIPTION

This application discloses a method and system for delivering nanoparticles into and through the skin, which can reduce the need for needles, micro-patches, chemical permeabilization of the skin, or other chemical or invasive procedures. In one embodiment, a magnetic field acts on nanoparticles placed on the skin's surface (in a gel, patch, or by other means), and transports them into and through the skin. The magnetic field can be applied by a magnetic injection system, where the magnetic injector device is placed above the particles. In another embodiment, it can be applied by a pull system placed below the particles, for example, acting through the width of a limb.

Specific embodiments provide methods, devices and systems for directing an active or therapeutic agent into and/or through skin. One exemplary embodiment is a device 1 for magnetically-assisted delivery of an active agent schematically shown in FIG. 5 (body part 1, patch 2, permanent magnet 3A, magnets 3B, patch with small magnets 3C, and magnetic forces 4). One operative principle for magnetically directing (e.g., with force F) the agent (or therapeutics) associated with magnetic particles (e.g. with $Fe_3O_4$ cores), which includes magnetizable nano-particles, involves an arrangement of magnets, which can have a North (N) and a South (S) pole, to direct magnetic-particle formulations or agents applied away from the targeted site (e.g. on the surface near the targeted site, or in the vicinity of targeted tissues) to the targeted site. Using this principle, the device with its plurality of magnets or magnetic elements can, for example, direct the agent from the fluid/gel solution to the target site. In this example the particles are "pushed" by the device. Alternatively, the parties can be pulled in an embodiment shown in FIG. 6 (permanent magnet 1, magnetic field lines 2, region of strong magnetic field 3, region of weaker magnetic field 4, force 5, chain of iron particles 6A, 6B).

In another embodiment, a method for treating a patient or animal comprises (a) placing a device proximal to the patient's dermis or skin, and (b) magnetically pushing an agent or active agent into or through the dermis or skin to a desired location within the patient or animal. This method can be used to push an active agent from surface of dermis or skin to a desired location therebelow. Such methods can be atraumatic, can deliver a therapeutically effective amount or a concentrated dose of the agent.

Another embodiment includes a device for delivering magnetizable agents to a treatment site. An arrangement of magnets creates a magnetic field that results in push forces, and these forces can be used to push in (magnetically inject) magnetic or magnetizable agents. More particularly, the device pushes outwards or magnetically injects magnetic or magnetizable carriers through skin or materials. Specifically, it creates forces on magnetic, paramagnetic, ferrimagnetic, ferromagnetic, or superparamagnetic materials, and transports them outwards from the device (e.g., the magnetic injector). In specific examples, the device can be configured for skin treatments.

Another embodiment includes methods for selecting magnets and magnetic nanoparticle formulations to enable magnetic drug delivery from the outside of the body, into and through the layers of the skin.

One exemplary device suitable with this method includes a device that includes a housing and a plurality of magnetic elements or magnets or magnetization that may be capable of generating magnetic fields. Typically, a single magnet can have field lines around it. The magnet can be set at an angle that creates a magnetic field along the horizontal x-axis at a desired location. A second magnet, with an opposite polarity, can be placed and angled in a configuration with respect to the first magnet so that the magnetic field is equal and opposite (along the minus x-axis) at the same desired location. The cancellation of the two fields can then create a node—a magnetic field zero or minimum. In one example, these two magnets are arranged such that the two magnetic fields overlap and can cancel at the location of the desired node point without canceling around that point. In one embodiment, a local magnetic field minimum can be created with a higher magnetic field surrounding the node. This creates magnetic forces, from regions of low to high magnetic field strength—from the node out—and thus push the magnetic or magnetizable agents away from the magnetic injection device.

Alternatively, an exemplary device suitable with this method includes a device having a housing and an electromagnet. The electromagnet may be capable of generating magnetic fields, which result in forces that can direct or push a therapeutic agent or other agent.

The plurality of magnetic elements is disposed in the housing and the magnetic field can have the effect to displace the agent from the outer to the middle skin, and can also direct it further into the skin, at a rate determined in part by the strength of the magnetic field. The magnetic device can push therapeutic agents into and through the skin.

In use and practice, active agents, including magnetic or magnetizable agents, can be for example magnetic nanoparticles coated with or containing drugs or other therapy, can be delivered from an initial location to another site (e.g., a treatment site) through the skin. For example, such agents can be placed on the skin as agents in a fluid (e.g. nanoparticles suspended in water), or agents in a gel, or as a powder, or as a paste, delivered in or via a flow, or by any other means that will reliably deliver them to a starting location on the skin. Then, the device is held in the vicinity of the magnetic or magnetizable agents, in such a way that the forces generated on the agents push the agents from the starting to a desired location or treatment site in or underneath the skin. This magnetic injection force can transport the agents through the skin.

The formulations of the pharmaceutical compounds or active agents that can be administered in connection with the methods comprise therapeutic agents, pharmaceutical agents (such as steroids, anti-inflammatory, or protectant agents), molecular agents, nucleotides, or proteins.

The agents or magnetic agents or therapeutic agents can be or can include therapeutics, drugs, proteins, or gene therapy, either by having these materials themselves be magnetic (e.g. a drug molecule that is magnetic or magnetizable), by incorporating magnetic materials either on a molecular basis (e.g. drug molecules that include iron) or by being bound or attached to magnetic materials. Magnetic agents that are made by placing magnetic materials inside or attaching them to non-magnetic objects (e.g. to starch or polymer objects, to/in micelles, liposomes, viruses, bacteria, cells) can themselves be therapeutic or can further contain therapeutics, drugs, proteins, or gene therapy on their surfaces or inside them. Non-magnetic agents (such as therapeutics, drugs, proteins, or gene therapy) can also be magnetically pushed by attaching them to or containing them inside agents that are or have been made magnetic. Binding, encapsulation, coatings, and other means may be chosen to select the therapy release rates (slow or fast), release times (immediately or after a certain duration), and conditions under which release will occur (pH, osmolarity, or other parameters) to most efficaciously treat target regions or locations. The agents may be formulated into powders, suspensions, gels, sprays, lotions, or other formulations known in drug delivery.

Therapeutics and drugs can include steroids (e.g. dexamethasone, prednisone, methylprednisolone, betamethasone), prostoglandins, anti-inflammatory agents, aminoglycosides, antibiotics (e.g. glycosides) or other drugs, and nucleotide or gene therapy. They can include target-specific ligands, linkers to other moieties, polar or non-polar moieties, and elements that can be used to help transport agents across physiological barriers.

Such pharmaceutical compositions can contain a therapeutically effective amount of active ingredients, and, as may be necessary, inorganic or organic, solid or liquid pharmaceutically acceptable carriers. Pharmaceutical compositions suited for topical/local administration to the inner skin include aqueous solutions or suspensions, which may either be ready to use or require preparation prior to use (e.g. lyophilisates). Suited pharmaceutical compositions further include gels, which may be biodegradable or non-biodegradable, aqueous or non-aqueous, or micro- or nano-sphere based. Examples of such a gel include, but are not limited to, carbomers, poloxamers, alginates, hyaluronates, xyloglucans, polyesters, polysaccharides, poly(lactides), poly(glycolide) or their co-polymers PLGA, sucrose acetate isobutyrate, and glycerol monooleate, whereas the gel may be formed in situ or prior to use from solutions or suspensions. These compounds further include creams and ointments, emulsions, micro-emulsions or self-emulsifying compositions. Pharmaceutical compositions suited for enteral or parenteral administration include tablets or gelatin capsules or aqueous solutions or suspensions as described above.

The agents, including pharmaceutical compositions, may be sterilized and/or may contain adjuvants, e.g. preservatives, stabilizers, wetting agents and/or emulsifiers, salts for regulating the osmotic pressure and/or buffers, penetration enhancers, bio-adhesive agents. The pharmaceutical compositions of the invention may, if desired, contain further pharmacologically active substances, such as, but not limited to antibiotics or analgesics. They may be prepared by any of the methods, e.g. by conventional mixing, granulating, confectioning, dissolving or lyophilizing methods, and contain from about 0.01 to 100% of active ingredient.

The amount to be administered may vary, depending upon the method of administration, duration of therapy, the condition of the subject to be treated, and the severity of the skin disease. In one example, the duration of therapy may range between one minute (or less) and several hours for a single treatment, and could be administered once or multiple times over a period of days, weeks, months, or years, and may extend up to chronic treatment. The therapeutically effective amount of the compound to be delivered may range between pico-grams to milligrams.

The agent should be magnetic or magnetizable (that is associated with magnetic materials). Magnetic materials suitable for site-directed delivery can be incorporated in the coating of an oral dosage formulation or inside the oral dosage formulation and used for site-directed delivery. Alternatively, the agent can be applied topically and then delivered to the targeted site. Further, the agent can be delivered intravenously and then delivered to the targeted site.

Magnetic materials can include paramagnetic, ferrimagnetic, ferromagnetic and superparamagnetic materials (e.g. iron containing compounds), martensitic stainless steels (e.g. 400 series), iron oxides (Fe2O3, Fe3O4), neodymium iron boron, alnico (AlNiCo), and samarium cobalt (SmCo.sub.5). Moreover, individual magnetic materials have been shown to possess properties that can be combined to achieve localized delivery. Ferromagnetic and superparamagnetic compounds include but are not limited to iron-containing compounds such as martensitic stainless steels (e.g. 400 series), iron and iron oxides (Fe2O3,Fe3O4).

If the agent is diamagnetic or if the magnetic material associated with the agent is diamagnetic, then the combined force from the device or system can attract the agent or associated diamagnetic material. Diamagnetic materials are slightly repelled by a magnetic field. Diamagnetic properties arise from the realignment of the electron orbits under the influence of an external magnetic field. The use of diamagnetic materials may reverse the interactions with the device or system.

In one exemplary embodiment, the magnetic material is in the form of nanometer, micron-sized or sub-micron-sized particles. Such particles may be incorporated in micro or nano-carriers, optionally the micro or nano-carriers contain an active agent to be delivered. Suitable sizes for the magnetic material range from nanometers up to sub-millimeters in cross-sectional diameter or width. In another exemplary embodiment, the magnetic material is larger than 10 nanometers in length, width, and/or diameter, and may have any shape (e.g. tubes, ellipses, etc.).

Magnetic particles may be incorporated into cells or attached to cell surfaces. In certain exemplary embodiments, magnetic particles may be fed to the target cells or temporary pores may be created in the cell membrane of the target cell by electroporation. In other exemplary embodiments, magnetic particles may be attached to the cell surface via an antibody binding to cell membrane receptors or through chemical conjugation of the magnetic particle to the cell membrane.

The iron-oxide nanoparticles that were originally placed on top of the skin, have travelled through the skin and have reached the location of blood vessels inside the skin. A person skilled-in-the-art of magnetism and therapy delivery would recognize that there are other alternatives to conducting the disclosed magnetic delivery of iron oxide into the skin, on other areas of the body, with other magnet sizes, placement, choice of particles, method of administration.

One or more agents may be formulated alone or with excipients or encapsulated on, in or incorporated into the microparticles or nanoparticles. Suitable agents include therapeutic, prophylactic, and diagnostic agents. These agents include organic or inorganic compounds, amino acids and proteins, sugars and polysaccharides, nucleic acids or other materials that can be incorporated using standard techniques.

In some exemplary embodiments, the magnetic fields may be provided in the form of one or more materials that are magnetic, i.e., that either exhibit a permanent magnetic field or that are capable of exhibiting a temporary magnetic field. The entire device, or selected portions thereof, may be manufactured from the one or more magnetic materials to provide a magnetic field generator. For example, a predetermined quantity of magnetite or an alloy thereof may be included in the construction of the device. Other materials may be utilized in addition to or in place of magnetite to provide the desired magnetic properties. Such materials may be temporary magnetic materials or permanent magnetic materials. Some examples of suitable magnetic materials include, e.g., magnetic ferrite or "ferrite", which is a substance consisting of mixed oxides of iron and one or more other metals, e.g., nanocrystalline cobalt ferrite. However, other ferrite materials may be used. Another example of a magnetic material is Neodymium, Cobalt, or other alloys of rare-earth elements.

Agents made from or contain magnetic, paramagnetic, ferrimagnetic, ferromagnetic, or super-paramagnetic materials. They can be of any shape or size, although spherical, elliptical, or rod shape agents are common, and they can have a variety of coatings. These agents will contain or be attached to therapeutics, or will themselves be therapeutic.

The sizes, shapes, and coatings of agents can be varied and selected based on application parameters. The magnetic force on an agent typically varies with the volume of magnetic or magnetizable materials in that agent. Thus, to increase magnetic forces, it is desirable to choose larger agents. However, larger agents may experience larger barrier resistance to motion—for the same magnetic force. Larger agents may also create more damage to skin as they move through it. For this reason, there can be a tradeoff: it may be suitable to pick agents that are big enough to experience sufficient magnetic forces but small enough to move through skin barriers easily and without causing undesirable damage. Agents may be selected to have coatings or surfaces that allow easier passage through skin barriers.

The magnetic forces created on agents by applied magnetic fields are known to a degree. For example, it is known that the magnetic force typically scales with the volume of magnetic or magnetizable material in the agent. Forces on agents can also be measured. Thus agents can be selected to provide a desired degree of magnetic forces. Inventive aspects of this disclosure include studies to select the most effective magnetic agents for into and through skin delivery.

Skin and tissue forces on agents, the forces that resist motion through skin barriers, may be accessed. Thus we disclose carrying out skin and animal experiments to measure skin/barrier resistance to agent motion as a function of agent size, shape, and coating. A sample experiment is to take agents of various sizes and measure their motion through skin samples or skin-mimic samples of specified thickness under a carefully applied magnetic field for a variety of agent shapes, sizes, and coatings. The data from such measurements can be used to determine skin resistance to agent motion for various agent sizes, shapes, and coatings. A measurement of the motion of the agent through skin may be used to assist in optimization. In contrast, magnetic forces on agents can be accurately predicted in many cases, but if/when they cannot, then experiments can be used instead.)

The composition of the particles (their size, surface charge, and the chemistry of any coatings), as well as the medium in which they are contained (the chemicals in a liquid buffer, or the properties of a gel, paste, or ointment that contains the particles) can increase or decrease the amount of delivery that is achieved by the applied magnetic field into and through skin. How these factors (size, charge, coatings, and medium composition) affect magnetic drug delivery is determined by complex inter-related physics and chemistry considerations and therefore the preferred particle and media composition is not obvious.

Increased particle size increases magnetic forces on each particle which is advantageous for magnetic drug delivery because it increases the force of delivery into and through skin; but at the same time an increased particle size also increases resistance to motion forces, both directly (larger particles experience larger viscous drag and skin resistance forces) and indirectly (larger particles create longer range magnetic attraction forces and aggregate more easily and quickly into larger aggregates which have a harder time passing through skin layers). Hence it is not obvious which particle size is best for magnetic drug delivery through the skin, as it depends on a competition between applied magnetic forces (bigger particles are better) versus resistance and aggregation (smaller particles are better).

In addition to size, selecting particle concentration also brings about competing physical effects, and it is not obvious how to select the best concentration. A low concentration of particles means that there are few particles available to deliver drug into and through the skin, and hence drug delivery will be limited. But conversely, a high concentration of particles leads to particle aggregation, to large aggregates, and to particles in front blocking particles behind them (a 'traffic jam' at the skin surface, similar to what would happen on a too busy highway at a toll center). Hence to maximize magnetic drug delivery into and through the skin there are considerations for particle speed (resulting from the strength of the applied magnetic field), aggregation, and obstruction and surface coverage by forward particles blocking particles behind them from entry. It is possible to set the concentration of particles too high, and to reduce the amount of drug delivered by exacerbating aggregation, blocking, and particle-to-particle interference issues. The best concentration of particles for maximum delivery into and through the skin is inter-dependent on magnetic field strength, particle type (different types aggregate and interact at different rates), on the chemistry of the media holding the particles, and is not obvious.

As for concentration, the optimal strength of the applied magnetic field and the magnetic gradient for maximal drug delivery into and through skin is also not obvious. Too small a magnetic field will have little effect on the particles, and there will be little motion and hence limited delivery through and into the skin. But too strong a magnetic field will cause aggregation and particle-to-particle blocking, which will increase the resistance of skin to particle motion and will lead to lower drug delivery. As above, how much magnetic field strength is best depends on the other factors, on particle size, composition, concentration, and on the chemistry of the media (liquid buffer, gel, paste, or ointment) that initially contains the particles.

As noted, another set of considerations that effect magnetic drug delivery into and through the skin is the chemistry of the media. The viscosity of the media initially containing the magnetic particles, plus additives to the media such as chemical shielding agents, surfactants, soaps, sugars and salts, and other excipients known to those familiar with drug delivery, can change how magnetic particles interact one with the other. Increasing media viscosity can increase the resistance to motion that magnetic particles will experience in the liquid buffer, gel, paste, or ointment media, but increasing media viscosity can also reduce how quickly particles come together and can limit particle-to-particle interactions to reduce the formation of aggregates (which may improve magnetic drug delivery into and through skin layers). Likewise, surfactants and soap media additives can modify particle-to-particle interactions, by modifying particle charge (thus for example increasing particle-to-particle electrostatic repulsion and thus reducing particle aggregation), by changing particle steric interactions, and by modifying the properties of the media and indirectly the magnetic particles. Media additives and excipients have a non-obvious effect on magnetic particle interactions, and thus a non-obvious effect on how those particles will interact one with another, how strongly or not they will form aggregates under the application of a magnetic field, and hence how effectively they will penetrate skin layers under the action of the applied magnetic field.

All of the above considerations, plus additional interactions that will be appreciated by those familiar with magnetic drug delivery (particle size distributions, particle shape, particle coatings, chemistry and pH changes as particles progress through various layers of the skin, change in magnetic field strength and gradient as the particles move relative to the magnets, etc), all of those can interact with each other and make it highly non-obvious to select the best formulation that will maximally deliver therapy into and through layers of the skin. Composition of the magnetic particles and the media that holds them (buffer, gel, paste, ointment, etc), as well as the design of the push or pull magnet devices, must be carefully and appropriately selected to match the strong resistance provided by the layers of the skin. Especially important is to select magnetic particle size, surface charge, coatings, and concentration, and the strength of the magnetic field and field gradient, to be able to penetrate the toughest layers of the skin—especially the outermost Stratum Corneum and the Epidermis layer with its tight cell-to-cell junctions.

In certain embodiments, the result of the method is an anti-aging effect on the portion of skin. In this regard, anti-aging or certain beneficial cutaneous agents may be applied using the magnetic device.

One advantage is specific methods allow for deliver drugs into and through the skin by using magnetic nanoparticles that are delivered into and through the skin by the application of a magnetic field. In this method there is no need, or at least less need, to mechanically puncture the skin with a needle.

EXAMPLES

The disclosure will be further described in connection with the following examples, which are set forth for purposes of illustration only.

Figure 2:
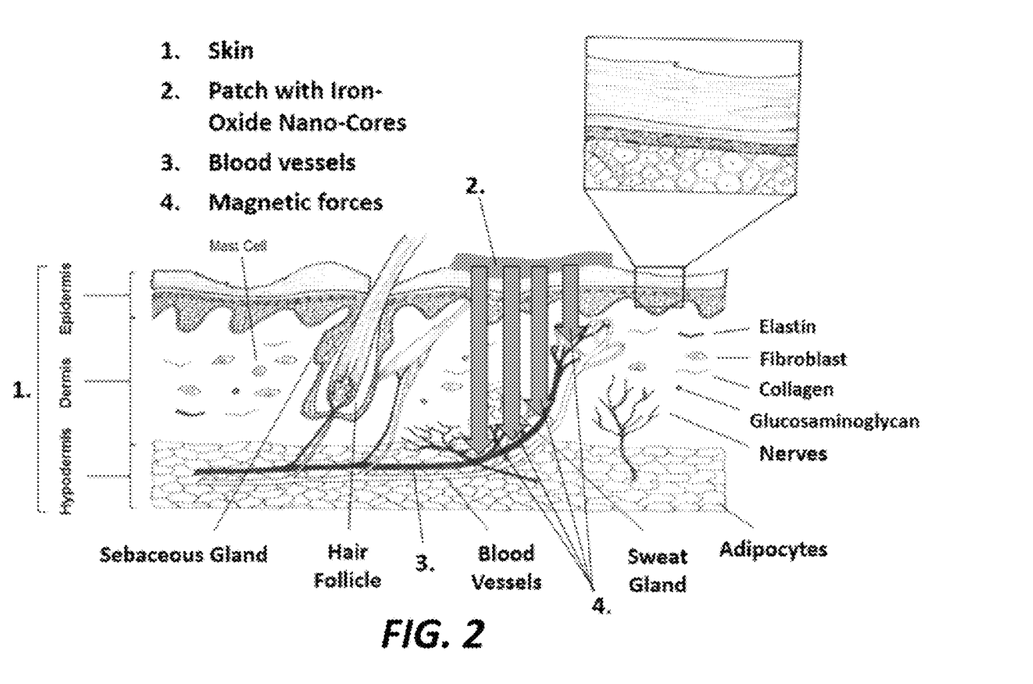
FIG. 2 illustrates one embodiment in which nanoparticles or agents are applied through a patch to skin.

FIG. 2 shows an exemplary formulation of nanoscale or micro-scale magnetic iron-oxide particles (with or without a coating) would be placed on the skin of the patient (for example on a patch of skin on the arm or foot) and then a magnet device would apply a force on the nanoscale or micro-scale iron oxide cores to transport them through the skin. If desired, the magnetic field may be applied for a sufficiently long time to transport the particles all the way to the blood vessel, thus achieving non-invasive delivery from the skin into the blood stream.

The magnetic forces can be applied by a magnet or magnets that are placed in the vicinity of the micro- or nanoparticles. Appropriately-chosen magnets can be placed either above the skin or below the limb or body part (e.g. a patch containing particles on the upper surface skin of a hand, arm, foot, leg or other body part, and then a magnet underneath the hand, arm, foot, leg or other body part). The magnet or magnets can be a permanent magnet(s), an electro-magnet(s), or a combination. The magnet can be applied below the limb to create pull forces, or a magnet system can be placed above the skin to push the particles into the skin. The push system can be a hand-held device, or can be composed of small magnets integrated inside a film, sheet, patch, or flexible or rigid cartridge that is placed directly on the skin. The magnet or magnets can apply a magnetic field that is constant in time, or a magnetic field that varies in time, so long as the magnetic field is selected so that the net force it applies on the iron-oxide particles is into and through the skin to the underlying blood vessels, as shown in FIG. 2.

Example 1

Figure 3:
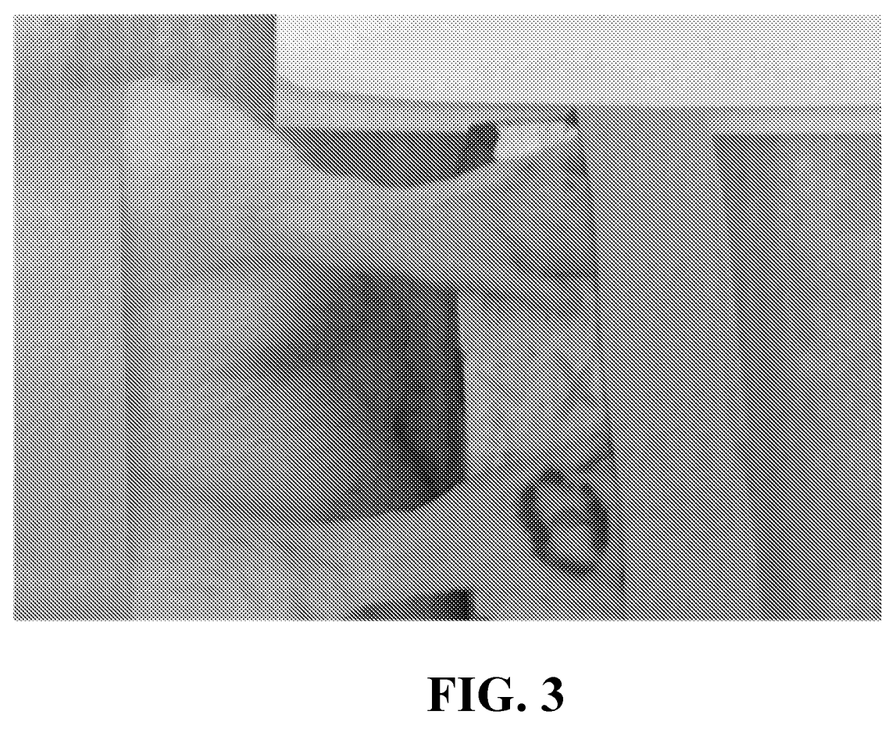
FIG. 3 shows a permanent magnet underneath the paws of a rat that can be used to deliver iron-oxide nanoparticles into and through the skin including to underlying tissue and blood vessels.

In this example and as shown in FIG. 3, a permanent magnet underneath the paws of a rat is used to deliver iron-oxide nanoparticles through the skin and to blood vessels. Rat paws were taped onto a 0.4 Tesla small rectangular magnet. The surface of the upper paws was cleaned with isopropanol and air dried. Then the center of the dorsal paw was marked with a marker. Four microliters (4 μL) of 10 nm diameter iron oxide nanoparticles with PEG coating were applied to the center of the marked circle. The magnet remained under the paws to draw the particles through the skin and into the blood vessels.

At the completion of magnet application, rats were terminated, the paws were cut off at the ankles, and placed into a tube with Fixative Decalcifier Formical-4 and put into the fridge at 4° C. until complete decalcification of the bones (to allow slicing of the foot to look at particle penetration). After decalcification, each paw was processed for paraffin embedding. The paraffin embedded paws were sectioned into 10 um thick slices (sliced perpendicular to the skin) and mounted onto microscope slides. These sections were stained for iron (Fe) with Perl's Prussian blue stain by using 10% potassium ferrocyanide. Every stained section was examined for presence of Prussian stain (blue), which indicated the location of the particles in the skin and underlying tissue.

Figure 4:
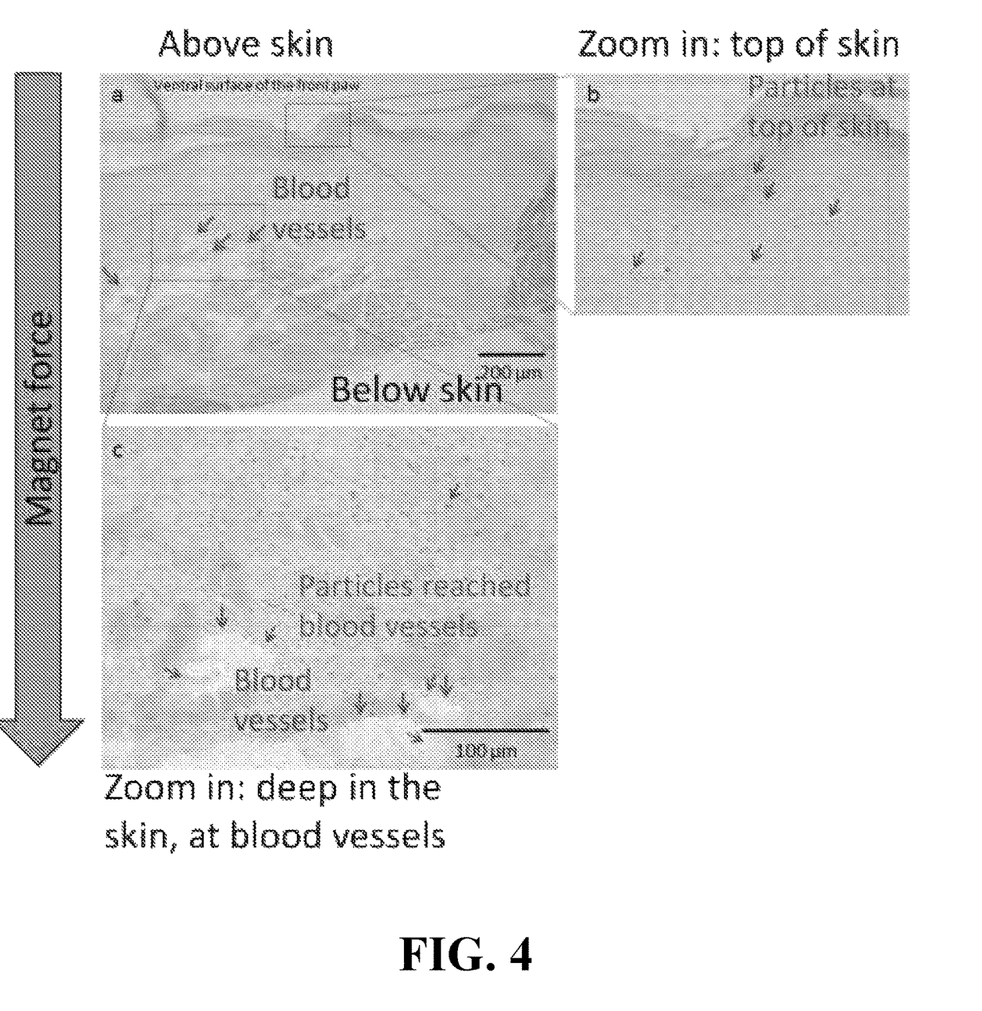
FIG. 4 depicts a sample skin cross-section from the experiment shown in FIG. 3.

A sample skin cross-section is shown in FIG. 4. Particle penetration into the skin under the applied magnetic field. A) Low-magnification cross-section through rat paw skin. Top of the image (ventral surface of the paw) is above the skin, bottom of the image is below the skin. The magnetic force acts from top to bottom (gray arrow). In this cross-section through the skin, the blood vessels are visible as white gaps in the skin and underlying tissue (and are marked by red arrows). b) Higher magnification zoomed-in view at the top of the skin. Iron-oxide particles were visualized by Perl's Prussian blue stain, are visible as blue dots, and are marked by the blue arrows. c) Higher magnification zoomed-in view deep inside the skin. The iron-oxide particles (blue dots marked by blue arrows) have reached the vicinity of the blood vessels (white gaps marked by red arrows).

FIG. 4 shows a representative cross-section through rat paw skin after magnetic delivery.

In the example above, particles were placed on the skin inside an aqueous (water-based) solution. A surrounding ring of wax or Vaseline or other substance that repels water can be used to contain the solution of particles when they are placed on the skin, and can essentially form a vessel on the skin into which a greater volume of solution can be applied (to deliver a higher dose of iron oxide). Particles can also be placed on the skin inside other liquids, for example inside an alcohol, an oil, or in another liquid. Some liquids can be advantageous either because they bring the particles closer to the skin (e.g. by surface tension effects), or arrange the particles in a desired configuration (e.g. in longer and more densely packed chains), or a specific choice of liquid may be advantageous because it may reduce the resistance of skin to particle motion. For example, some liquids are known to act as skin permeabilizors, they typically reduce the resistance of the top layer of skin (the stratum corneum), e.g. by temporary disruption of the highly ordered "brick-and-mortar" tile structure of the stratum corneum cells. Particles can also be placed on the skin as bare particles (sprinkled or in powder form). Particles can also first be enclosed inside a patch, membrane, gel, paste, ointment, bandage, or by other means to apply them effectively to the skin before magnetic forces are then applied.

Example 2

Figure 5:
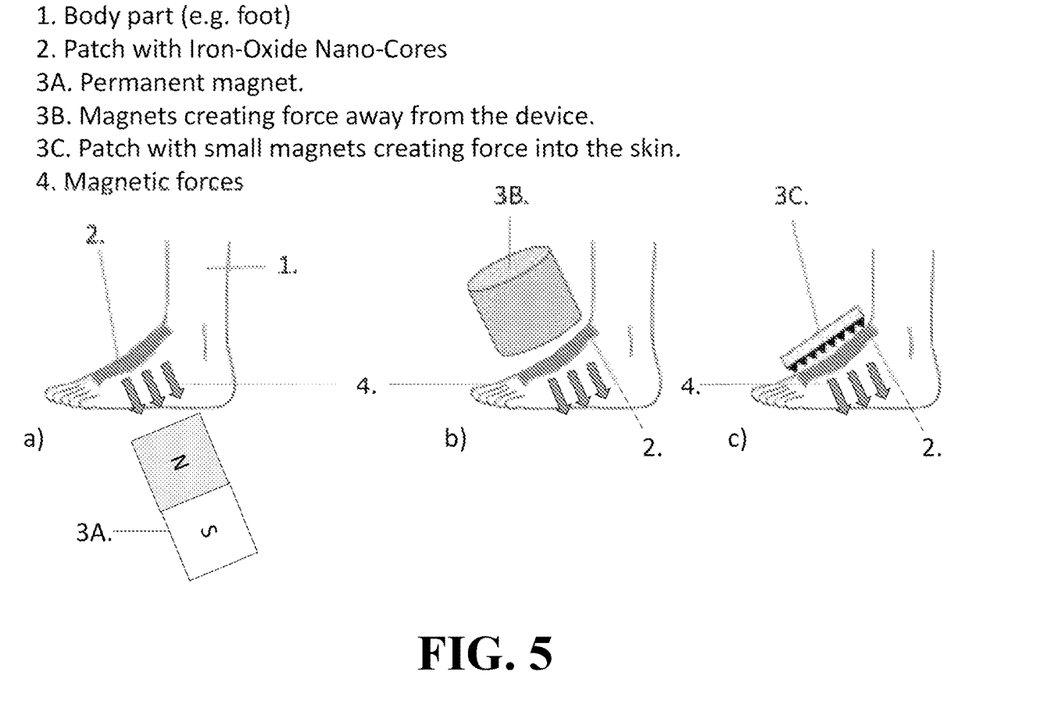
FIG. 5 depicts an exemplary embodiment in which the particles are driven by pushing the particles through the skin on a foot.

Magnet Configurations: This application includes placing a magnet underneath the magnetic (e.g. iron-oxide) particles to direct them through the skin. This application also discloses placing a configuration of magnets above the particles, to push them into the skin. Such a configuration of magnets could be in a device held close to the skin (FIG. 5b) or the device itself could be placed directly on the skin in a film, sheet, or patch (as in FIG. 5c). If the magnet device is placed directly on the skin, the particles could be placed on the skin before the magnet device is applied, or the placement of particles could be integrated with and into the magnet device (for example as a thin cartridge that is slid into the magnet device immediately before application onto the skin).

There are exemplary methods of arranging magnets (permanent, electromagnetic, or a combination thereof) to most effectively direct particles through the skin and into underlying blood vessels. For instance, it is advantageous to arrange the magnet or magnets such that the magnetic field is along the direction of travel of the particles, that way the chains of particles will align with their intended motion and will act more like "arrows" moving through the skin.

Example 4

Figure 6:
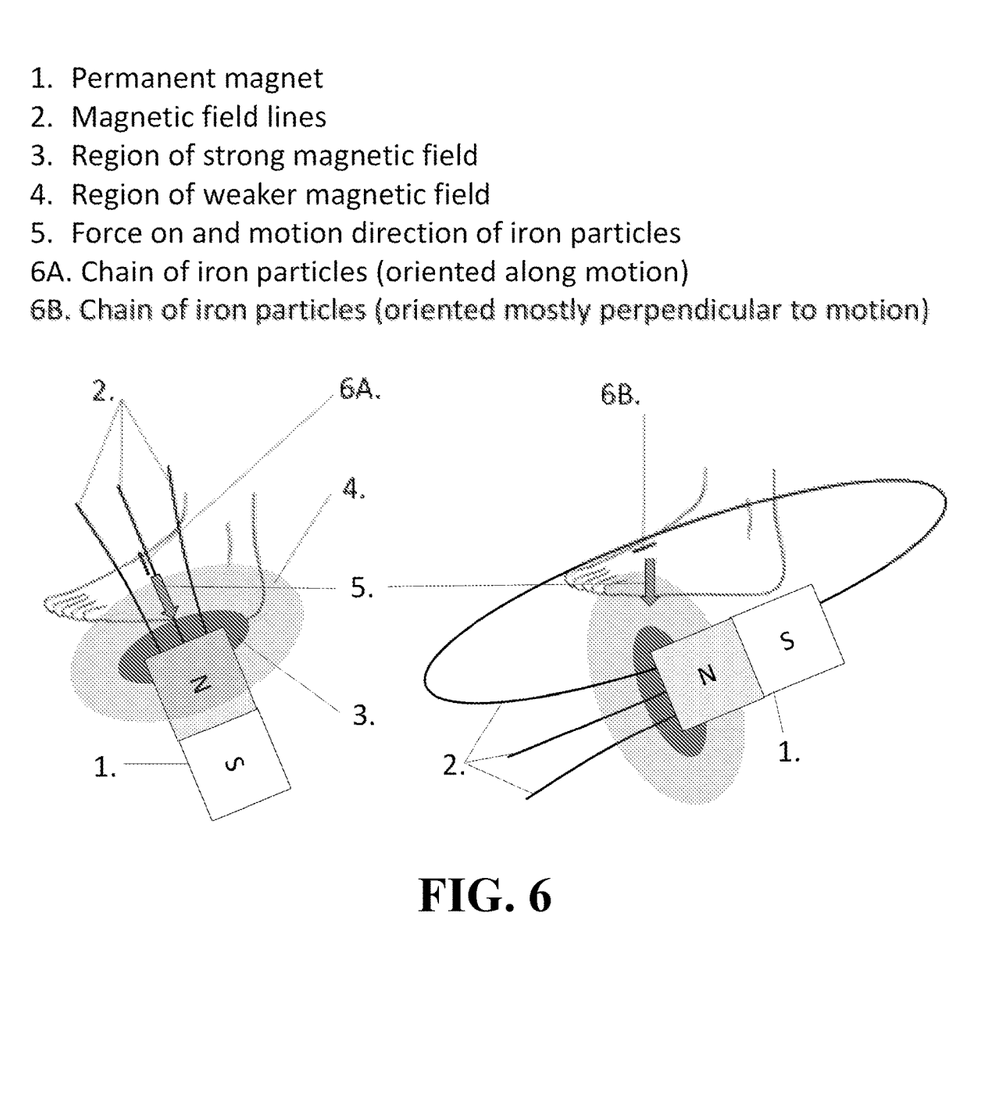
FIG. 6 depicts a depicts an exemplary embodiment in which the particles are driven by pulling the particles through the skin on a foot.

FIG. 6 shows an exemplary arrangement of magnetic fields by proper magnet placement. A) Advantageous magnetic field and magnetic gradient. The resulting chains are lined up like arrows along their intended motion. B) Less effective magnet arrangement, now the chains are aligned perpendicular to their intended motion and their ability to move through skin is reduced.

Example 4

This application also includes a magnetic patch or the use thereof. Someone versed in the art of magnetic fields will recognize that small magnets close to the particles can create stronger forces than larger magnets placed further away. Since for magnetic injection into the skin, it is possible to place the magnets right up against the particles and the skin, it can be advantageous to use small magnets inside a thin film (a magnetic patch), as shown in FIG. 5C, label 3C. A patch, sticker, bandage, or film could contain both magnetic nanoparticles with attached therapy and a collection of many small magnetic injectors. This combined magnets+particles system could be applied as a convenient patch to the skin to deliver the particles+therapy into the skin. We disclose such an integrated magnet+particles patch system for delivery of therapy into and through the skin.

In one or more embodiments, nanoparticles can have a diameter is between about 200 nm to about 400 nm. In other embodiments, nanoparticles can have a diameter is between about 10 nm to about 800 nm. Nanoparticles can be introduced as an active agent.

Example 5

Inventive experimental studies were conducted to select particle size, concentration, applied magnetic field strength, and media additives for best drug delivery through skin layers. FIG. 3 describes a study for magnetic delivery of nanoparticles through intact skin in paws of live rats. This study used a strong permanent magnet places as close to the particles as possible (just under the paws of the rat), and very small magnetic particles (10 nm in diameter). Hence it tested one limit of the skin magnetic drug delivery design space (smallest particles, strong and nearby magnet creates a high magnetic field and gradient) for effective magnetic delivery into and through the skin. This is one inventive embodiment that enables magnetic delivery into and through the skin. To select other embodiments, to begin to map the skin magnetic drug delivery space, the following additional experimental studies were also conducted.

Figure 7:
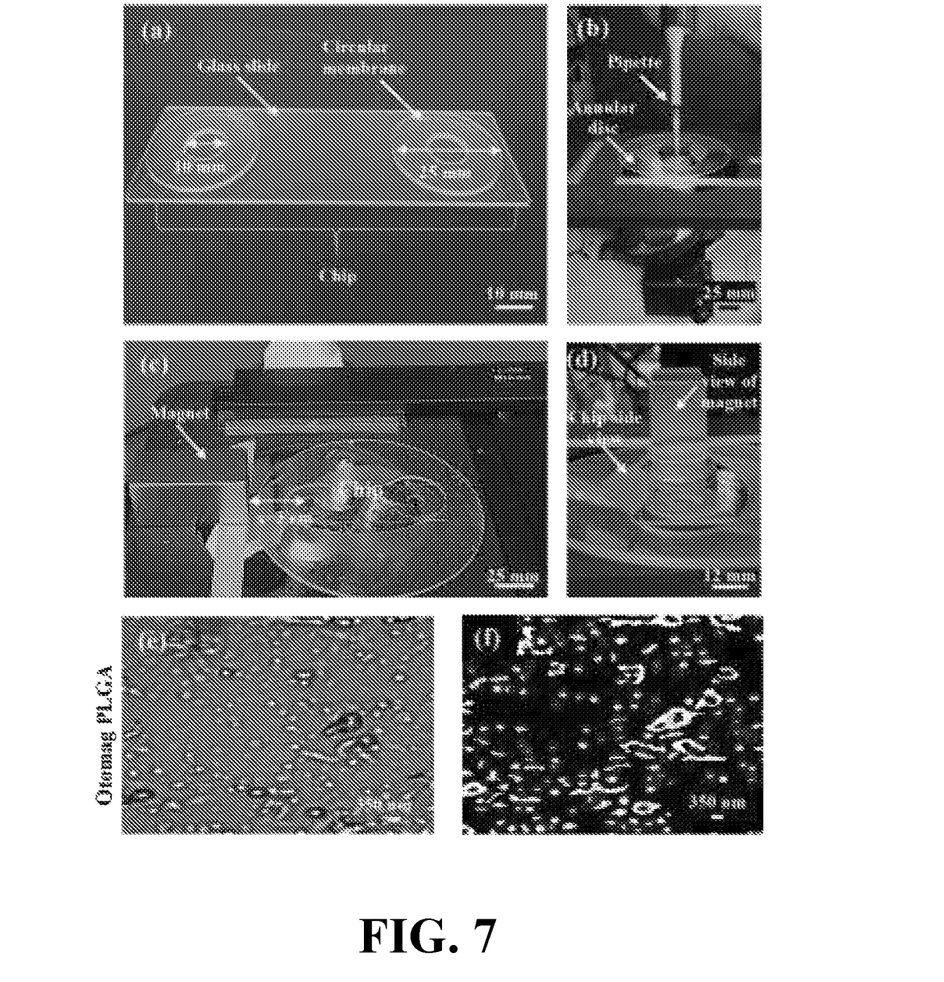
FIG. 7 shows an experimental setup having a chip assembly

FIG. 7 shows an experimental setup having (a) Chip assembly consisting of circular membrane glued on a glass slide. (b) Magnetic particles solution being placed in the chip via pipette. (c) The chip on a confocal microscope with the magnet and (d) side view of the chip on a confocal microscope with the magnet. (e) Snapshot of raw image of the magnetic particles (images at 40× objective zoom). (f) The images are processed in Matlab. A threshold is applied, and the centroids of distinguishable micro-particles or nanoparticle aggregates are marked by red circles (images at 40× objective zoom).

The speed of magnetic particles in viscous media determines how much drug can be delivered per time. If the particles move faster under the application of a magnetic field, then there is more drug being delivered per unit time (delivery flux=concentration×speed=amount delivered per area per second). This speed is a function not only of the size and composition of the magnetic particles and the strength of the applied magnetic field and gradient, but it also depends on particle aggregation. As the magnetic particles aggregate into chains-like structures, the magnetic force and viscous resistive drag experienced by the aggregates changes with their length and composition, and thus the resulting speed of motion also changes. A test system was designed to measure particle aggregation and speed of motion under the application of a calibrated magnetic field strength. The micro-fluidic test system consisted of a glass chip placed under a microscope. A magnetic field was applied by a permanent magnet whose size and distance from the particles can be selected to create magnetic fields and gradients of different strengths. These strengths were predicted by mathematical simulations and then confirmed by Hall probe measurements, so that the applied strengths were known and had been calibrated ahead of time. Videos of particle motion were recorded. And image processing codes were written and implemented to quantify aggregate length and the speed of motion of aggregates (how quickly aggregates were seen to move from frame to frame in the video). A photograph of this experimental setup is shown in FIG. 7.

Example 6

Figure 8A:
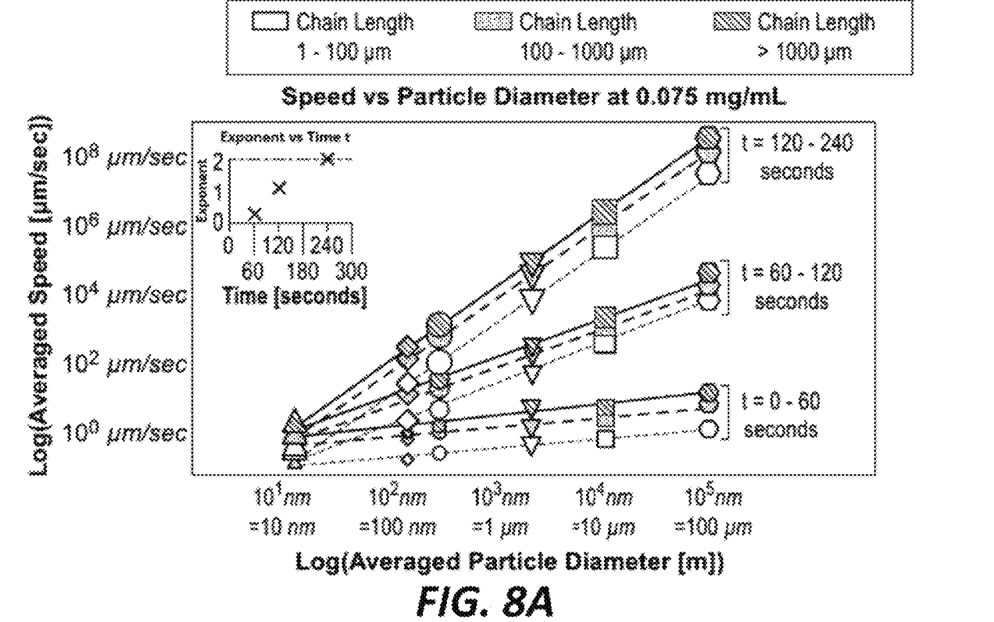
FIGS. 8A-8C show data show particle speed in viscous media versus particle size and concentration.
Figure 8B:
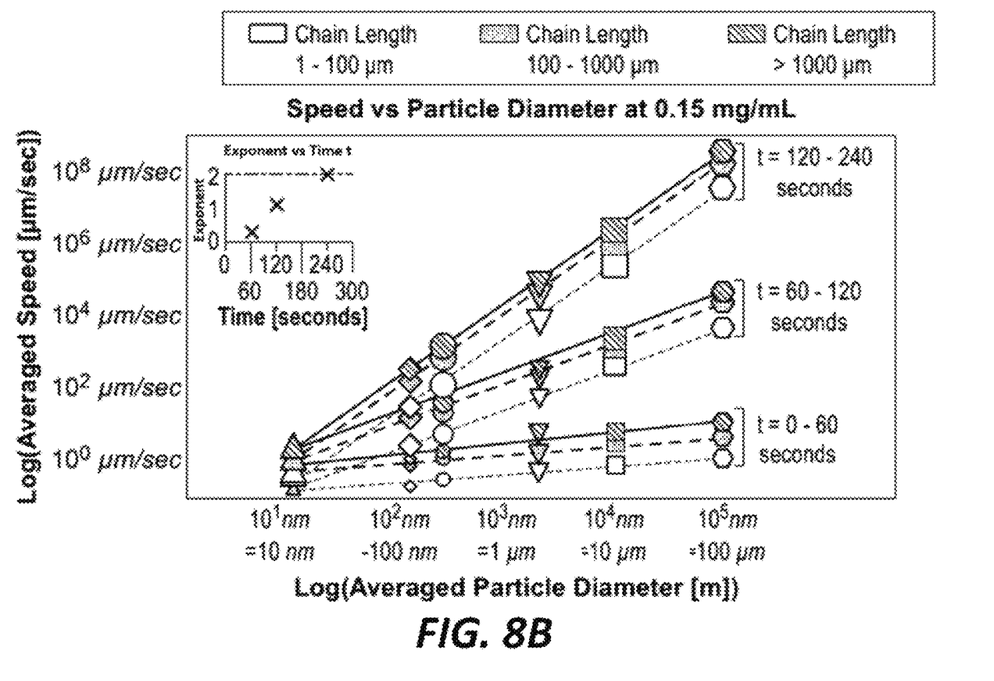
Figure 8C:
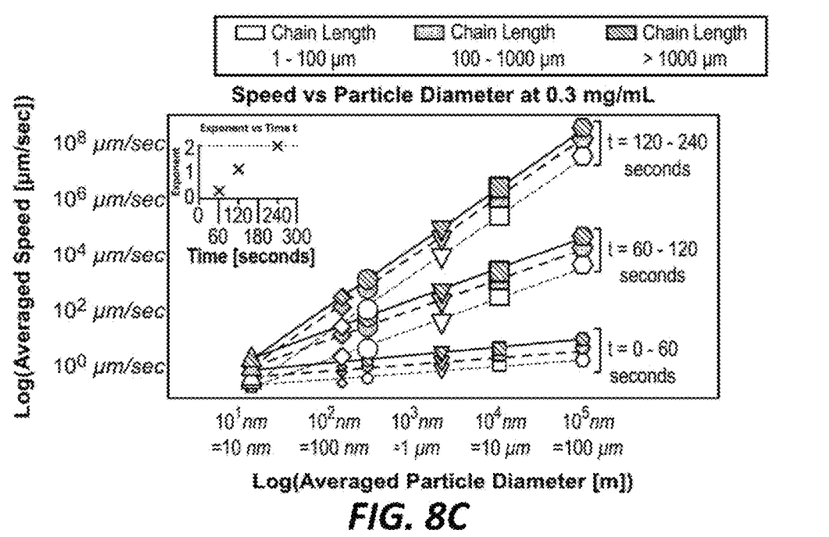

FIGS. 8A-8C show data show particle speed in viscous media versus particle size and concentration. FIGS. 8A, 8B, and 8C show that magnetic nanoparticle speed versus particle diameter for t=0-240 sec. Different magnetic particles are denoted by different symbols. For each particle type, speed was measured at three different concentrations, i) at 0.075 mg [iron]/mL, ii) at 0.15 mg [iron]/mL, and ii) at 0.3 mg [iron]/mL. Measurements were conducted in triplicate for each condition. A linear regression fit is provided for each time period (R2 values were 0.2 to 0.3 at t=0-60 sec, 1 to 1.1 at 60-120 sec and 2.0 at 120-240 sec).

Power-relations were observed for particle size and particle concentration versus resulting aggregate speed. These power-relation fits provide an understanding of the physics of magnetic nanoparticle aggregate motion under the influence of an applied magnetic field and opposing viscous forces. Specifically, the outcomes from these sets of experiments were as follows. Larger magnetic particles moved faster. And particles at higher concentrations created longer aggregates and moved faster. As aggregates formed and particle speed reached a maximum, this maximum speed of the chain or needle-like aggregates was proportional to the square of the diameter of the particles tested ($V \sim d^2$). At long times, the length of the aggregates was linearly proportional to the diameter of the particles ($L \sim d$). The speed of particle aggregates was observed to be proportional to the square of the length of the chain or needle-like aggregates ($V \sim L^2$). This understanding of how aggregate speed varies with particle size and particle concentration was used to design the next set of inventive experiments, and to inform the selection of the best particle selection for maximum drug delivery through skin layers.

Example 7

The above studies on aggregate motion provided a first inventive understanding on how to select particle size, concentration, and magnetic field configurations to maximally deliver into and through skin layers. However, these experiments did not yet include a barrier layer. Another set of studies was conducted that include an added barrier in the micro-fluidic microscopy setup. This barrier was an agarose gel whose density and pore size can be controlled, and for this set of studies a tightly cross-linked agarose gel was used to mimic the tough barrier represented by skin layers. This study focused on assessing how particle concentration and magnetic field strength influence transport through a skin-like barrier. The results were surprising and non-obvious, see FIG. 9.

These experiments were carried out to assess the magnetic field strength and magnetic particle concentration that would enable best penetration through a skin-like densely cross-linked agarose barrier in a microfluidic testbed. Under the action of the magnetic field the magnetic nanoparticle form chain-like aggregates. The study tested the combination of magnetic field strength (vertical axis) and particle concentration (horizontal axis) that achieved different delivery efficiencies through the skin-like barrier. A non-obvious result was that there was a concentration threshold (bold thick line in FIG. 9) that was magnetic field dependent and beyond which the transport efficiency (% markings) was significantly reduced. A further non-obvious aspect was that this threshold was lowest (left most) at the low magnetic field strength, potentially because a stronger magnetic field has an increased ability to push through the skin-like barrier. If this concentration threshold was due to aggregate size only, then dependence would have been reversed (the lower magnetic field creates smaller aggregates). Hence the interaction between the magnetic field, aggregates, and penetration through the barrier is inter-related and non-obvious. This data can be converted into delivery numbers by multiplying the delivery efficiency (the percentage above each panel) by the concentration, thus giving an indication of the total amount of magnetic particles delivered through the skin-like barrier. Therefore this study provide information on which magnetic field strength and concentration may be best for magnetic delivery through the skin, as marked by the 'best choice' and '2nd best choice' notations in the plot.

Figure 9:
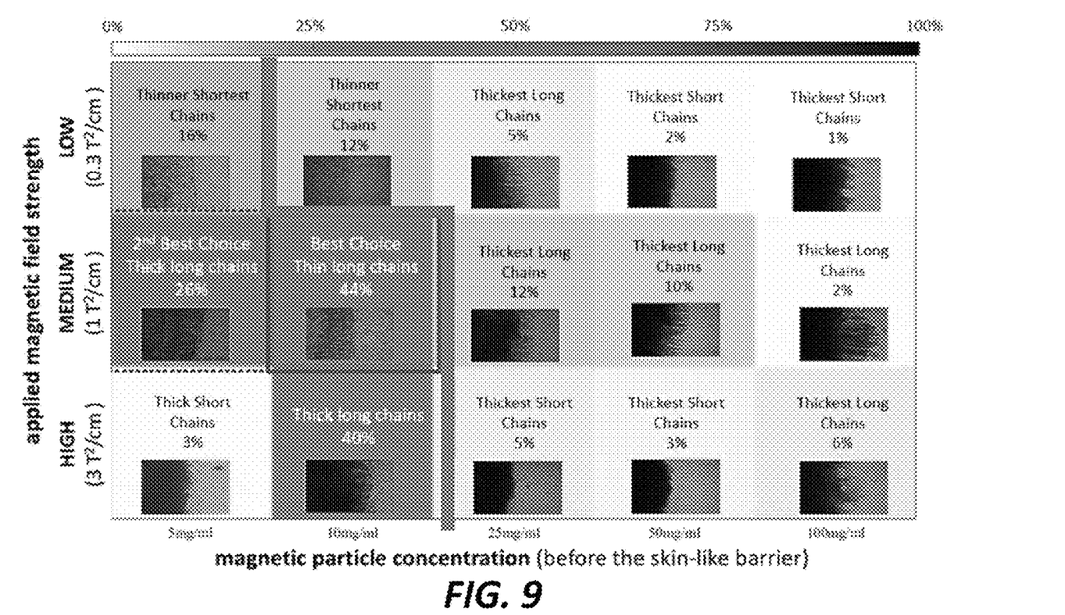
FIG. 9 shows data for penetration through a skin-like barrier for various magnetic field strengths and magnetic particle concentrations.

FIG. 9 shows experiments to determine a best applied magnetic field strength and particle concentration for penetration through a skin-like barrier in a microfluidic testbed. Under the action of the magnetic field the magnetic nanoparticle form chain-like aggregates. This experiment tested the combination of magnetic field strength (vertical axis) and particle concentration (horizontal axis) that achieved different delivery efficiencies through the skin-like barrier. A non-obvious result was that there was a concentration threshold (bold thick line) that was magnetic field dependent and beyond which the transport efficiency (% markings) was significantly reduced. A further non-obvious aspect was that this threshold was lowest (left most) at the low magnetic field strength, potentially because a stronger magnetic field has an increased ability to push through the skin-like barrier. If this concentration threshold was due to aggregate size only, then dependence would have been reversed (the lower magnetic field creates smaller aggregates). Hence the interaction between the magnetic field, aggregates, and penetration through the barrier is inter-related and non-obvious. To convert this data into delivery numbers, multiplying delivery efficiency (the percentage above each panel) by the concentration gives an indication of the total amount of magnetic particles delivered through the skin-like barrier. Hence this study provide information on which magnetic field strength and concentration may be best for magnetic delivery through the skin, as marked by the 'best choice' and '2$^{nd}$ best choice' notations in the plot.

The barrier experiments above used a densely cross-linked agarose gel as the skin-line barrier. Another set of experiments was done with a layer of cells grown in such a way that the cell-to-cell junctions were tight (as verified by patch clamping). Magnetic nanoparticles were placed above this cell layer, and then a calibrated magnetic field was used to transport the particles through these cell layers. These cell layers were a better representation of the tight-cell junctions barrier in the epidermis layer of the skin.

FIG. 9 shows the resulting data that indicates that particle sizes on the two extremes, small (26 nm diameter) and quite large (201 nm diameter), were able to penetrate this tight-junctions cell layer that mimics the epidermis of the skin. A potential reason for this is that at intermediate sizes, there are different competing effects (e.g. magnetic force through versus resistance to aggregate motion by the barrier) all of medium-size strength, and the resulting delivery is modest. The indication that there is more than one regime (a small and a large particle size) where through skin delivery is effective.

Example 8

Figure 10:
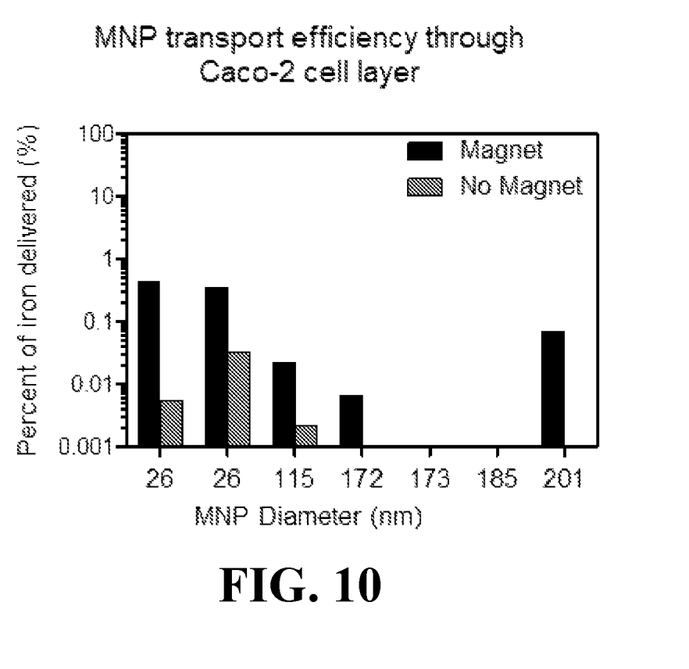
FIG. 10 shows the percent of magnetic particle delivery through a layer of cells with tight cell-to-cell junctions, and this figure shows data that indicates that particle sizes on the two extremes small (26 nm diameter) and large (201 nm diameter) were able to penetrate this tight-junctions cell layer that mimics the epidermis of the skin.

FIG. 10 shows the percent of magnetic particle delivery through a layer of cells with tight cell-to-cell junctions. Such a cell layer mimics the composition of the epithelial barrier layer in skin. The amount of particles delivered through this barrier was measured by Inductively Coupled Plasma Mass Spectrometry (ICP-MS).

The Examples of the present application have been described with reference to the accompanying drawings, but the present application is not limited to the Examples and may be fabricated in various forms, and it will be understood by a person with ordinary skill in the art to which the present application pertains that the present application may be implemented in other specific forms without modifying the technical spirit or essential feature of the present application. Therefore, it is to be appreciated that Examples described above are intended to be illustrative in every sense, and not restrictive.

Although specific embodiments of the invention have been described above in detail, the description is merely for purposes of illustration. It should be appreciated, therefore, that many aspects of the invention were described above by way of example only and are not intended as required or essential elements of the invention unless explicitly stated otherwise. Modifications of, and equivalent steps corresponding to, the disclosed aspects of the exemplary embodiments, in addition to those described above, can be made by a person of ordinary skill in the art, having the benefit of this disclosure, without departing from the spirit and scope of the invention defined in the following claims, the scope of which is to be accorded the broadest interpretation so as to encompass such modifications and equivalent structures.

What is claimed:
1. A system for directing a therapeutic agent into a skin comprising:
   magnetizable nanoparticles, acted on by a magnetic field to direct the magnetizable nanoparticles into and through the skin, wherein the magnetizable nanoparticles may be one or more of ferro, ferri, paramagnetic, or super-paramagnetic nanoparticles; and a water repellant substance, placed on the skin, to contain the therapeutic agent, wherein the water repellant substance bounds the therapeutic agent.

2. The system of claim 1, wherein the therapeutic agent is directed into or through the skin.

3. The system of claim 1, wherein the magnetic field is applied by a magnetic injection device.

4. The system of claim 1, wherein the magnetic field is applied by a magnetic pull device.

5. The system of claim 1, wherein the nanoparticles comprise at least one of: loaded with therapeutic agents, drugs, proteins, or genes, or any combination thereof.

6. A method for treating a patient comprising:
providing a delivery device capable of generating a magnetic field;
placing the device above, below or aside to a patient's skin;
placing a therapeutic agent within a bounding water repellant substance that is placed on the skin to contain the therapeutic agent; and
directing the therapeutic agent into the patient's skin via the device, wherein the therapeutic agent is directed to a treatment site.

7. The method as claimed in claim 6, wherein the therapeutic agent is magnetic, superparamagnetic, ferrimagnetic, ferromagnetic, or paramagnetic.

8. The method as claimed in claim 6, wherein the therapeutic agent is combined with a material that is magnetic, superparamagnetic, ferrimagnetic, ferromagnetic, or paramagnetic.

9. The method as claimed in claim 8, further comprising the step of pushing the therapeutic agent from a surface of the patient's skin into the skin.

10. The method as claimed in claim 6, further comprising the step of pulling the therapeutic agent.

11. The method as claimed in claim 6, wherein an effective amount the therapeutic agent is pushed into the patient's skin by the magnetic field.

12. The method as claimed in claim 6, wherein the therapeutic agent is biodegradable.

13. The method as claimed in claim 6, wherein the device comprises a plurality of magnetic elements in which at least two magnetic elements are arranged at an angle.

14. The method as claimed in claim 6, further comprising the step of placing the therapeutic agent within a middle layer of the patient's skin.

\* \* \* \* \*